United States Patent [19]

Nakamori et al.

[11] Patent Number: 5,270,009
[45] Date of Patent: Dec. 14, 1993

[54] METHOD OF AND APPARATUS FOR MEASURING OXYGEN CONCENTRATION WITH LIMITING CURRENT OXYGEN SENSOR

[75] Inventors: Akioki Nakamori; Masaru Kozakura, both of Kyoto, Japan

[73] Assignee: Shimadzu Corporation, Kyoto, Japan

[21] Appl. No.: 942,407

[22] Filed: Sep. 9, 1992

[30] Foreign Application Priority Data

Sep. 27, 1991 [JP] Japan .................. 3-276660

[51] Int. Cl.$^5$ ............................................. G01N 27/00
[52] U.S. Cl. ..................................... 422/83; 73/31.01;
 73/23.21; 73/1 G; 73/23.31; 422/98
[58] Field of Search ................... 422/83, 98; 73/23.21,
 73/23.31, 1 G, 31.01; 364/571.01, 556, 551.01

[56] References Cited

U.S. PATENT DOCUMENTS

| | | | |
|---|---|---|---|
| 3,718,434 | 2/1973 | Pierce | 422/83 |
| 4,377,801 | 3/1983 | Weber et al. | 73/23.31 |
| 4,418,566 | 12/1983 | Beck et al. | 73/23.31 |
| 4,553,424 | 11/1985 | Sakurai et al. | 73/23.2 |
| 4,578,762 | 3/1986 | Wong | 422/83 |
| 4,630,038 | 12/1986 | Jordan | 73/1 G |
| 4,779,446 | 10/1988 | Rowland | 73/1 G |
| 4,816,800 | 3/1989 | Onaga et al. | 73/23.31 |
| 4,852,384 | 8/1989 | Woolbert et al. | 73/1 G |
| 5,017,340 | 5/1991 | Pribat et al. | 73/23.31 |
| 5,065,613 | 11/1991 | Lehnert et al. | 422/83 |

*Primary Examiner*—Robert J. Warden
*Assistant Examiner*—Hien Tran
*Attorney, Agent, or Firm*—William L. Klima

[57] ABSTRACT

Relation of the degree of interference to interference concentration is previously stored with respect to at least one interference gas influencing an oxygen indicated value of a sample gas, so that interference corresponding to interference gas concentration of the sample gas is corrected on the basis of the stored relation when oxygen concentration is calculated from a detection signal of an oxygen sensor and outputted. Concentration of the interference gas, with respect to which the relation of the degree of interference is stored, is manually inputted in measurement, or previously set. When the concentration of the interference gas is previously set, such concentration is made changeable by manual input. Thus, even if the sample gas contains an interference gas in high concentration as in the case of an exhaust gas containing highly concentrated $CO_2$ gas, it is possible to accurately measure oxygen concentration of the sample gas.

4 Claims, 4 Drawing Sheets

METHOD OF AND APPARATUS FOR MEASURING OXYGEN CONCENTRATION WITH LIMITING CURRENT OXYGEN SENSOR

BACKGROUND OF THE INVENTION

1. Field of the Invention

The present invention relates to a method of and an apparatus for measuring oxygen concentration in a sample gas with a limiting current oxygen sensor, and more particularly, it relates to measuring method and apparatus which are suitable for measuring oxygen concentration in a sample gas, such as an exhaust gas, for example, containing a great deal of an interference gas.

2. Description of the Background Art

A limiting current oxygen concentration measuring apparatus is provided with a limiting current oxygen sensor comprising electrodes which are formed on both sides of a stabilized zirconia member. When a voltage is applied across the cathode and the anode of the oxygen sensor during bringing a sample gas into contact with the cathode, a current flows through carriers of oxygen ions contained in the sample gas by pumping action of the stabilized zirconia member. Thus, oxygen contained in the sample gas is discharged toward the anode through the stabilized zirconia member. At this time, the current becomes constant with respect to the oxygen concentration of the sample gas in a certain range of the voltage across the electrodes. Such a constant current is called a limiting current. Since the oxygen concentration has linear relation to the limiting current, it is possible to detect the oxygen concentration by measuring the value of the limiting current.

A limiting current oxygen sensor employing such a principle is generally adapted to measure oxygen concentration in a clean gas, or a gas which is approximate in composition to the atmospheric gas. When the sample gas is an exhaust gas from an automobile or a factory and contains $CO_2$ in high concentration, however, $CO_2$ serves as an interference gas for oxygen in the oxygen sensor to hinder correct measurement of oxygen concentration. In general, therefore, the oxygen sensor is not employed for measurement of a gas such as an exhaust gas containing $CO_2$ in high concentration.

When $CO_2$ contained in a sample gas having high $CO_2$ concentration is absorbed by an absorbent in order to measure oxygen concentration with the oxygen sensor, the composition of the sample gas is so changed that oxygen concentration cannot be correctly attained in a sampling point.

In the aforementioned oxygen sensor, further, it is necessary to limit the inflow of oxygen molecules by some means. When the inflow is limited by a small hole, for example, no problem is caused in measurement of a gas which is substantially unchanged in spun gas composition. If a gas containing a great deal of foreign gas molecules, such as those of $CO_2$ contained in an exhaust gas, in percentage order, however, physical properties of the sample gas are so changed that an indicated value of oxygen concentration cannot be correctly attained.

SUMMARY OF THE INVENTION

An object of the present invention is to provide a method and an apparatus which can accurately measure oxygen concentration in a sample gas with a limiting current oxygen sensor, even if the sample gas contains an interference gas, such as highly concentrated $CO_2$ gas contained in an exhaust gas, in high concentration.

According to the inventive method of measuring oxygen concentration, the degree of relation of interference to interference gas concentration is previously stored with respect to at least one interference gas influencing an oxygen indicated value of a sample gas, so that interference corresponding to interference gas concentration of the sample gas is corrected on the basis of the stored relation when oxygen concentration is calculated from a detection signal of an oxygen sensor and outputted. Concentration of the interference gas, with respect to which the degree of relation of interference is stored, is manually inputted in measurement, or previously set. When the concentration of the interference gas is previously set, the same is made changeable by manual input.

On the other hand, the inventive apparatus for measuring oxygen concentration comprises an oxygen concentration detector formed by a limiting current oxygen sensor, a gas inlet path having an inflow gas switching valve for switching constant volumes of a calibration gas and sample gas for introducing the same into the oxygen concentration detector, a memory unit storing relation of the degree of interference to interference gas concentration with respect to at least one interference gas influencing an oxygen indicated value of the sample gas, and an arithmetic processing part for correcting interference corresponding to concentration of the interference gas contained in the sample gas with respect to a detected value of the oxygen concentration detector on the basis of the relation stored in the memory unit.

According to a preferred aspect of the present invention, the apparatus for measuring oxygen concentration further comprises an input unit, so that concentration of the interference gas can be manually inputted.

In one of the fields to which the inventive method and apparatus are applied, oxygen concentration of an exhaust gas from an automobile or a factory is measured. Such an exhaust gas contains $CO_2$ gas as the interference gas. FIG. 2 shows interference of $CO_2$ against oxygen concentration which is detected by a limiting current oxygen sensor, in the form of deviation rates (%) with respect to indicated values of oxygen concentration to $CO_2$ gas concentration (volume percent throughout the specification). Interference of $CO_2$ results in indicated values of oxygen concentration which are lower than actual values. Since it is known that an exhaust gas contains about 5 to 15% of $CO_2$ gas, $CO_2$ gas concentration is set at 10%, in order to measure such an exhaust gas. Thus, detected values of oxygen concentration are shifted by 1.25% toward higher sides, to be outputted. It is understood that interference of $CO_2$ in oxygen sensor can be suppressed within about ±1% by this simple correction method, if $CO_2$ gas concentration is in a range of 5 to 15%.

If the sample gas contains $CO_2$ gas in concentration of 20%, it is possible to correct indicated values of oxygen concentration by re-setting $CO_2$ concentration at 20% through the input unit.

In order to apply the inventive apparatus for measuring oxygen concentration to an exhaust gas measuring apparatus, $CO_2$ gas concentration may be previously set at 10%, so that this $CO_2$ gas concentration is re-set through the input unit only when a gas containing $CO_2$ gas in concentration being extremely out of 10% is measured.

DESCRIPTION OF THE PREFERRED EMBODIMENTS

Figure 1:
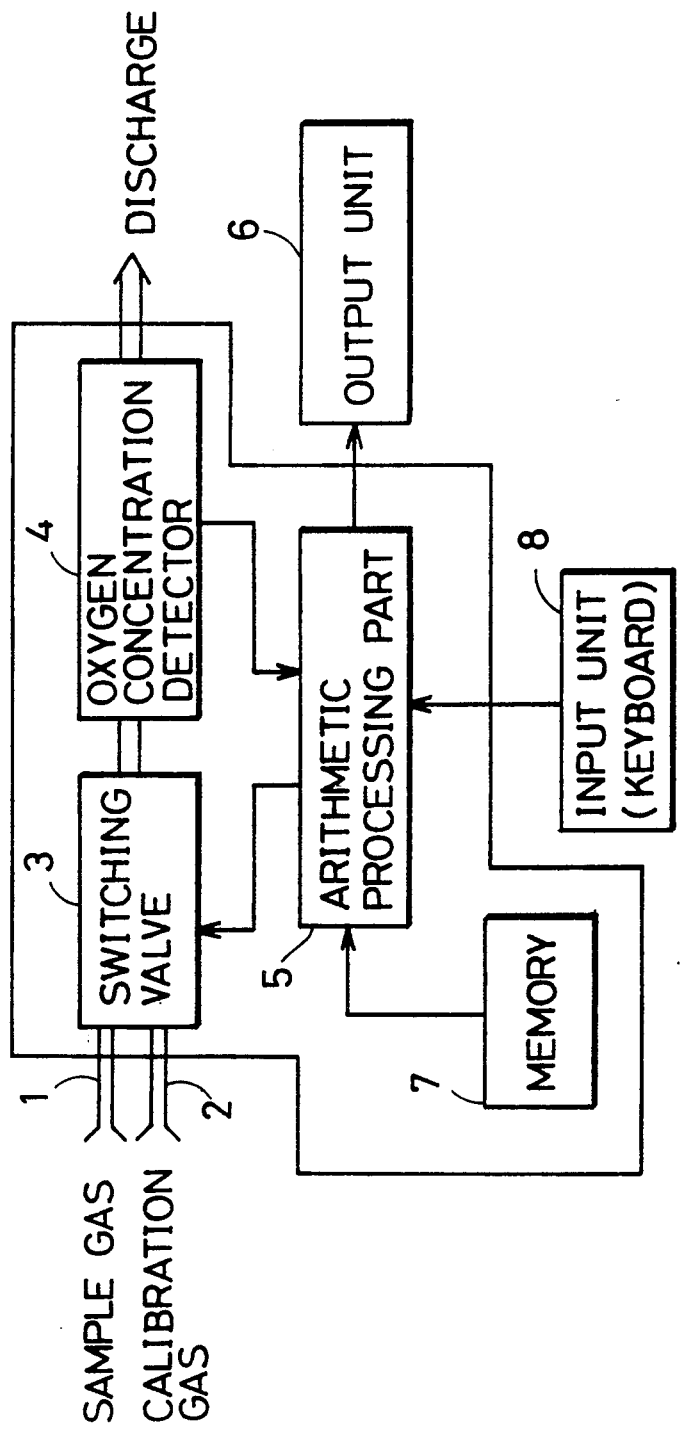
FIG. 1 is a block diagram showing a limiting current oxygen concentration measuring apparatus according to the present invention.

FIG. 1 is a block diagram showing the structure of a limiting current oxygen concentration measuring apparatus according to the present invention. Referring to FIG. 1, a sample gas inlet path 1 and a calibration gas inlet path 2 are connected to an inflow gas switching valve 3, which in turn switches a sample gas and a calibration gas and guides the same to an oxygen concentration detector 4 which is formed by a limiting current oxygen sensor. The sample gas inlet path 1, the calibration gas inlet path 2 and the switching valve 3 define a gas inlet path. A memory unit 7 is adapted to store relation between interference gas concentration and the degree of interference with respect to an interference gas which influences an oxygen concentration indicated value of the sample gas. An arithmetic processing part 5 including a CPU (Central Processing Unit) is adapted to control the operation of the switching valve 3, as well as to output on oxygen concentration value of the sample gas to an output unit 6 by a concentration signal from the detector 4. It is indicated that the sample gas contains an interference gas, the arithmetic processing part 5 outputs a corrected oxygen concentration value to the output unit 6 using a correction system as described later and the relation of interference stored in the memory unit 7. The output unit 6 is formed by a display unit such as a CRT (cathode ray table), a printer, or a recorder. An input unit 8 such as a keyboard is adapted to set $CO_2$ concentration of the sample gas with respect to the arithmetic processing part 5 and change the same.

Figure 4:
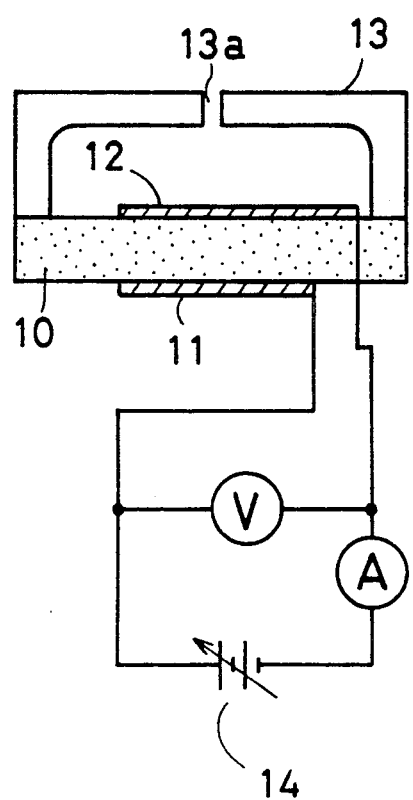
FIG. 4 is an end view schematically showing the principle of a limiting current oxygen sensor employed in an embodiment of the present invention.

FIG. 4 shows the limiting current oxygen sensor which is applied to the oxygen concentration detector 4. Referring to FIG. 4, the limiting current oxygen sensor comprises a solid electrolytic member 10 of zirconia ($ZrO_2$) which is stabilized by a solid solution of $Y_2O_3$ or CaO, platinum paste electrodes 11 and 12 which are formed on both sides of the solid electrolytic member 10, and a cap 13, having a small hole 13a, which is connected to one side of the solid electrolytic member 10 provided with the electrode 12. When a voltage is applied from a power source 14 so that electrode 12 serves as a cathode and the other electrode 11 serves as an anode, a current flows through carriers of oxygen ions by pumping action of the solid electrolytic member 10, to discharge oxygen contained in the cap 13 from the electrode 12 toward the other electrode 11. The applied voltage from the power source 14 is so adjusted that the current flowing in the solid electrolytic member 10 reaches a limiting current value which has linear relation to oxygen concentration in the cap 13.

Figure 3:
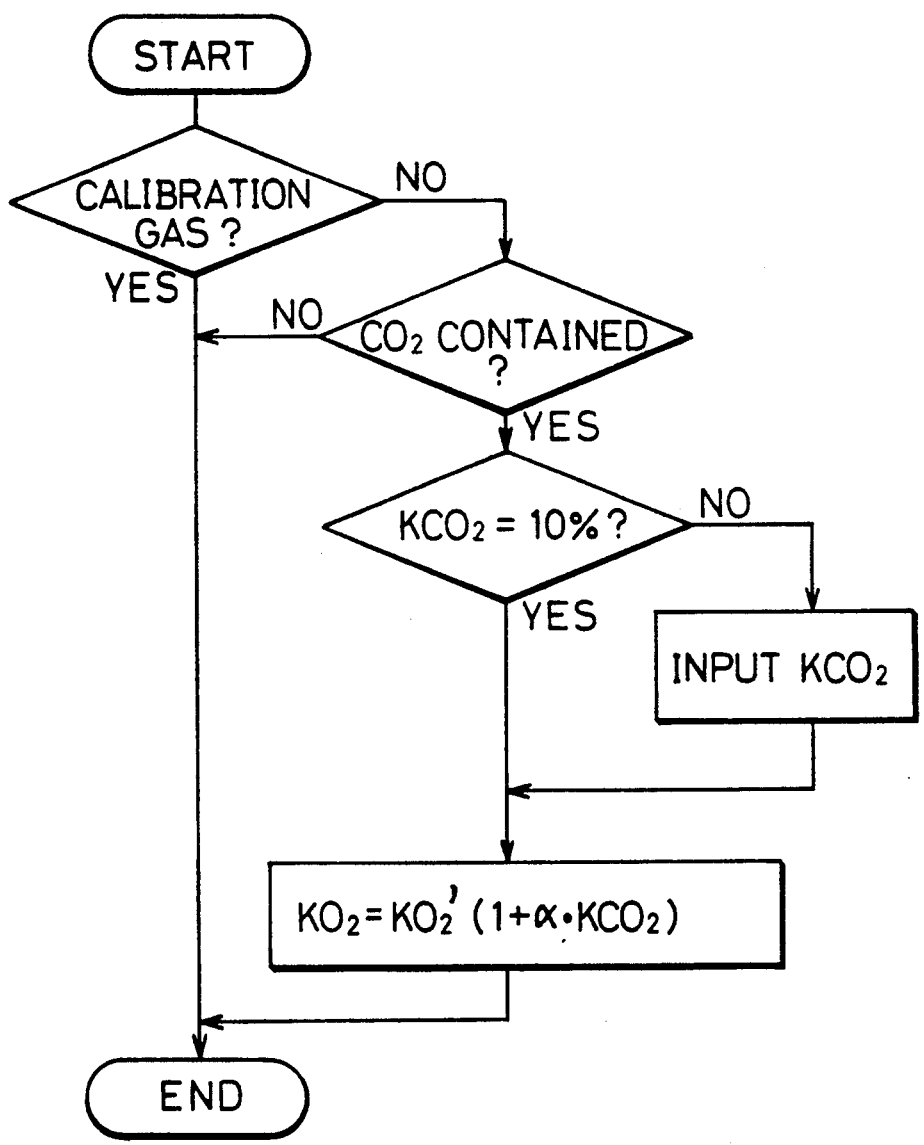
FIG. 3 is a flow chart showing the procedure of measuring oxygen concentration in a gas containing $CO_2$ gas with the inventive apparatus.

With reference to FIG. 3, description is now made on the procedure of detecting and correcting oxygen concentration in a sample gas with the oxygen concentration measuring apparatus shown in FIG. 1.

(1) It is inputted that the inlet paths 1 and 2 are for sample and calibration gases respectively, so that constant volumes of sample and calibration gases are introduced into the switching valve 3 from the sample and calibration gas inlet paths 1 and 2 respectively, and a start switch is turned on.

(2) The arithmetic processing part 5 controls the switching valve 3, and makes a determination as to whether or not the inflow gas is the calibration gas, depending on whether the switching valve 3 is switched toward the sample gas or the calibration gas. If the inflow gas is sample gas, a determination is made as to whether or not $CO_2$ gas is contained. This determination is made along previous setting or manual input made by a measurer through the input unit 8.

Figure 2:
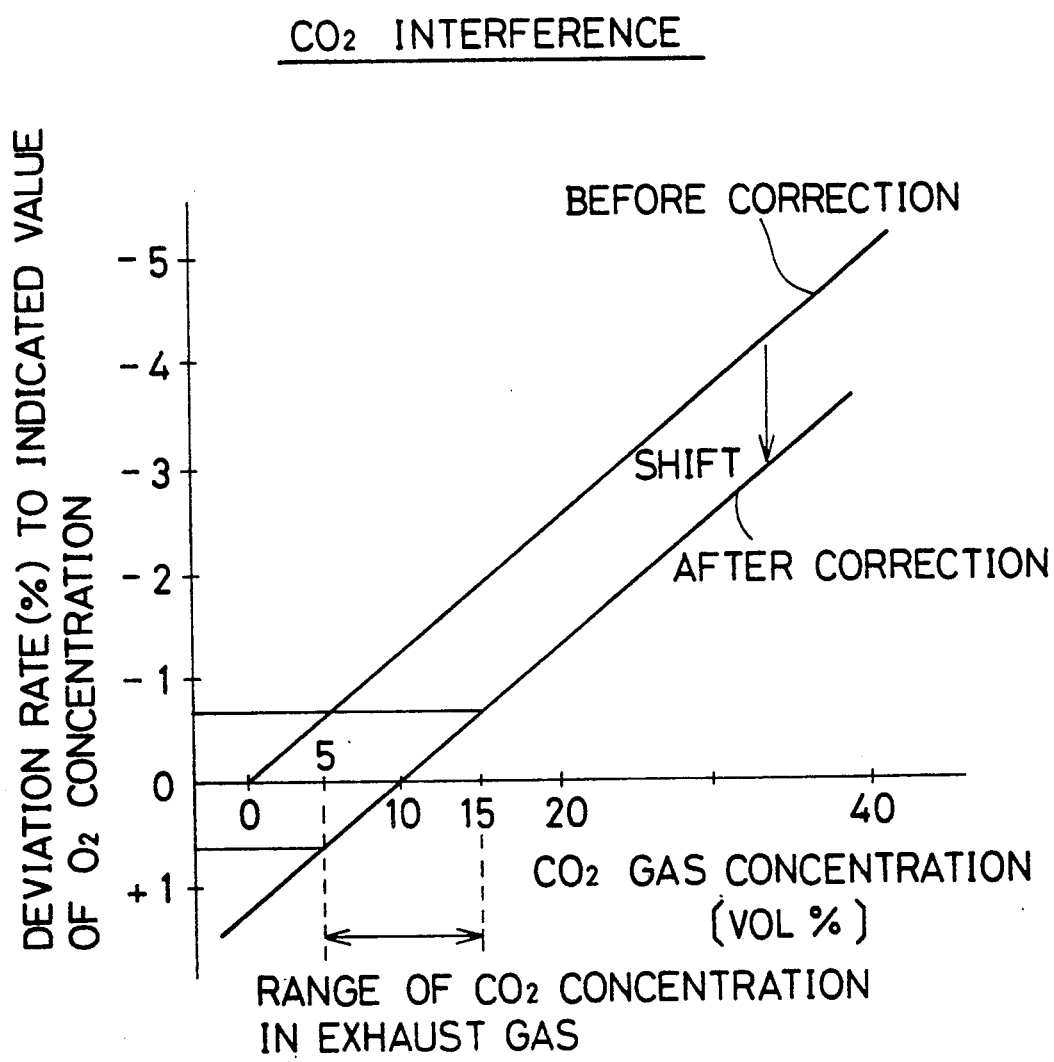
FIG. 2 is a graph expressing $CO_2$ interference in relation to an oxygen sensor, in the form of deviation rates (%) of oxygen concentration indicated values with respect to $CO_2$ gas concentration before and after correction.

(3) Assuming the $CO_2$ concentration in the sample gas is set at 10% in the measuring apparatus for measuring an exhaust gas, it is assumed that $CO_2$ gas concentration is 10% when a determination is made that $CO_2$ gas is contained, unless the measurer inputs $CO_2$ concentration other than 10%. If $CO_2$ gas concentration other that 10% is inputted, a corrected value obtained by shifting a deviation value shown in FIG. 2 is outputted along the inputted $CO_2$ concentration. The operation for this correction is made along the following expression:

$$KO_2 = KO_2'(1 + \alpha \cdot KCO_2)$$

where $KO_2$ represents $O_2$ concentration after correction, $KO_2'$ represents $O_2$ concentration before correction, $KCO_2$ represents $CO_2$ concentration in the sample gas, and $\alpha$ represents the degree of influence of $CO_2$ interference which takes the value shown in FIG. 2 by $CO_2$ concentration.

(4) If the sample gas contains no $CO_2$ gas, the measured value is directly outputted with no correction.

(5) If a determination is made that the inflow gas in the switching valve 3 is the calibration gas, no correction is made but the switching valve 3 is switched toward the sample gas side by the arithmetic processing part 5, and the start switch is again turned on.

If $CO_2$ gas concentration in the sample gas is known, high accuracy correction is enabled by carrying out the correction not with the previously set value of 10% but with $CO_2$ gas concentration changed to the known concentration.

Although the arithmetic processing part 5 is formed by a CPU in the above description, correction may be analogously made by an electric circuit, in place of such a CPU.

As to a gas, other than $CO_2$ gas, which is contained in a sample gas in a great deal to change gas physical properties, it is possible to make correction similarly to that for $CO_2$ gas, as an interference gas influencing measurement of oxygen concentration, to output a measured oxygen concentration value.

When an oxygen concentration indicated value influenced by an interference gas such as $CO_2$ gas is not corrected as in the prior art, it is impossible to correctly measure oxygen concentration of a sample gas such as an exhaust gas containing a great deal of $CO_2$. According to the present invention, on the other hand, it is possible to measure oxygen concentration in relatively high accuracy with simple correction means.

Although the present invention has been described and illustrated in detail, it is clearly understood that the same is by way of illustration and example only and is not to be taken by way of limitation, the spirit and scope of the present invention being limited only by the terms of the appended claims.

The features disclosed in the foregoing description, in the claims and/or in the accompanying drawings may, both, separately and in any combination thereof, be material for realising the invention in diverse forms thereof.

What is claimed is:

1. A limiting current oxygen concentration measuring apparatus, comprising:
   a sample gas supply;
   a calibration gas supply;
   an oxygen concentration detector formed by a limiting current oxygen sensor;
   a gas switching valve connected between said sample gas and calibration gas supplies and said oxygen concentration detector for selectively switching calibration gas and sample gas containing at least one interference gas for introducing the same into said oxygen concentration detector;
   a memory unit storing a relation of degree of interference to interference gas concentration of at least one interference gas influencing an oxygen indicated value of said sample gas; and
   an arithmetic processing part for correcting interference corresponding to concentration of said interference gas with respect to a detection value of said oxygen concentration detector on a basis of said relation stored in said memory unit.

2. An apparatus in accordance with claim 1, further comprising an input unit for manually inputting concentration of said interference gas.

3. An apparatus in accordance with claim 1, wherein concentration of said interference gas is previously set in said arithmetic processing part,
   said apparatus further comprising an input unit for inputting said concentration of said interference gas, so that interference gas concentration is manually inputted from said input unit for changing said concentration when concentration of said interference gas contained in said sample gas is different from said previously set concentration.

4. An apparatus in accordance with claim 1, wherein said arithmetic processing part is connected to said gas switching valve for selectively controlling the introduction of sample and calibration gases.

* * * * *